United States Patent
Erl et al.

(10) Patent No.: US 9,938,493 B2
(45) Date of Patent: Apr. 10, 2018

(54) SINGLE-USE CELL CULTURE CONTAINER

(71) Applicant: Sartorius Stedim Biotech GmbH, Göttingen (DE)

(72) Inventors: Wolfgang Ludwig Erl, Hagelstadt (DE); Joseph Seidl, Arnstorf (DE)

(73) Assignee: SARTORUIS STEDIM BIOTECH GMBH (DE)

( * ) Notice: Subject to any disclaimer, the term of this patent is extended or adjusted under 35 U.S.C. 154(b) by 237 days.

(21) Appl. No.: 14/403,433

(22) PCT Filed: May 23, 2013

(86) PCT No.: PCT/EP2013/001525
§ 371 (c)(1),
(2) Date: May 19, 2015

(87) PCT Pub. No.: WO2013/174515
PCT Pub. Date: Nov. 28, 2013

(65) Prior Publication Data
US 2015/0247113 A1     Sep. 3, 2015

(30) Foreign Application Priority Data
May 24, 2012   (DE) .................. 10 2012 010 155

(51) Int. Cl.
*C12M 1/00*   (2006.01)
*A61L 2/08*   (2006.01)

(52) U.S. Cl.
CPC ............. *C12M 23/14* (2013.01); *A61L 2/081* (2013.01); *C12M 23/28* (2013.01); *C12M 47/16* (2013.01)

(58) Field of Classification Search
CPC ...... C12M 23/28; C12M 23/26; C12M 37/00; A61L 2/081
See application file for complete search history.

(56) References Cited

U.S. PATENT DOCUMENTS

| | | | |
|---|---|---|---|
| 5,730,933 A | 3/1998 | Peterson | |
| 6,391,638 B1* | 5/2002 | Shaaltiel | C12M 23/14 435/289.1 |
| 2006/0246537 A1* | 11/2006 | Jenkins | C12M 23/14 435/68.1 |
| 2006/0280645 A1 | 12/2006 | Sellers et al. | |
| 2007/0071798 A1 | 3/2007 | Herweck et al. | |
| 2011/0092726 A1* | 4/2011 | Clarke | C12M 21/02 554/175 |

FOREIGN PATENT DOCUMENTS

| | | |
|---|---|---|
| DE | 69530386 | 6/1995 |
| DE | 202007005399 | 4/2007 |
| EP | 1072274 | 1/2001 |
| EP | 1430831 | 6/2004 |
| EP | 1481693 | 12/2004 |
| EP | 1598086 | 11/2005 |
| EP | 1589925 | 4/2009 |
| WO | 2006034157 | 3/2006 |

* cited by examiner

*Primary Examiner* — Jonathan M Hurst
(74) *Attorney, Agent, or Firm* — Colin P. Cahoon; Shaukat A. Karjeker; Carstens & Cahoon, LLP

(57) ABSTRACT

A method for producing a single-use cell culture container at least partially made of polymer material, wherein the cell culture container is treated with gamma radiation for sterilization, characterized in that the cell culture container is treated with inert gas and/or a defined amount of oxygen before the irradiation in order to prevent the occurrence of an "extended lag phase".

2 Claims, 3 Drawing Sheets

Figure 5 (Table 1)

Composition mg/L

| | |
|---|---|
| L-Arg HCl | 188.33 |
| L-Asn H$_2$O | 127.42 |
| L-Cys HCl H$_2$O | 44.00 |
| L-Gln | 87.50 |
| Gly | 14.58 |
| L-His HCl H$_2$O | 46.29 |
| L-Ile | 22.35 |
| L-Leu | 57.75 |
| L-Lys HCl | 70.42 |
| L-Met | 18.11 |
| L-Phe | 18.71 |
| L-Pro | 37.08 |
| L-Ser | 13.13 |
| L-Thr | 44.84 |
| L-Trp | 25.11 |
| L-Tyr | 23.72 |
| L-Val | 61.74 |

| inorganic salts | | vitamins | | other components | |
|---|---|---|---|---|---|
| CaCl$_2$·2H$_2$O | 56.68 | Biotin | 0.01 | D-glucose | 1700.00 |
| FeSO$_4$·7H$_2$O | 3.11 | Ca-pantothenate | 2.83 | Hypoxanthine | 10.00 |
| | | Choline chloride | 45.00 | | |
| KCl | 199.10 | Myo-inositol | 15.17 | Linoleic acid | 0.07 |
| | | Folic acid | 2.33 | | |
| MgSO$_4$·7H$_2$O | 158.38 | Niacinamide | 1.98 | Thioctic acid | 0.18 |
| NaCl | 6955.00 | Pyridoxine HCl | 2.18 | Phenol red | 2.67 |
| NaHCO$_3$ | 2100.00 | Riboflavin | 0.40 | Putrescine | 0.27 |
| Na$_2$HPO$_4$ | 182.30 | Thiamine HCl | 1.46 | Na-pyruvate | 91.67 |
| ZnSO$_4$·7H$_2$O | 0.74 | Vitamin B$_{12}$ | 0.88 | Thymidine | 2.00 |

SINGLE-USE CELL CULTURE CONTAINER

BACKGROUND

1. Field of the Invention

The present invention inter alia relates to a method for producing of a single-use cell culture container.

2. Description of the Related Art

Such cell culture containers are well known in the art and are at least partially made from polymer material. The known cell culture containers may be constructed from multiple layers, wherein the inner layer, i.e. the layer which gets into contact with the cell cultures, is made of a polymer material. Usually at least this layer consists of polyethylene (PE) or ethyl-vinyl acetate (EVA).

A single-use cell culture container is a container which may be used for the biopharmaceutical or other production of peptides, proteins, antibodies or other bacterial, microbiological or cellular products in large amounts. Said process is also named fermentation and so-called bioreactors are used for this fermentation process. In the context of the described invention a single-use cell culture container, which is usually formed of a polymer material in the form of a bag for producing large amounts of biological materials, may also be called a disposable bioreactor. In the following text the term cell culture container means any shape of a single-use cell culture container or disposable cell culture container or bag or bioreactor for the production of biomaterials.

Before filling the known cell culture containers, which are in particular present in the form of cell culture bags, these containers are treated with gamma radiation for sterilization. This treatment is required in order to kill all microorganisms, which may disturb or affect an optimal cell growth. The sterilization is usually done such that a plurality of cell culture containers is introduced into a radiation device. Subsequently, the cell culture containers are treated with gamma radiation.

SUMMARY

It has been found that with many of the above-described single-use cell culture containers the growth of cell cultures or bacterial or microbial cultures is compromised. In particular, a so-called "extended lag phase" is frequently observed, namely a delayed growth of the cells or organisms to be cultured. Such an "extended lag phase" is particularly undesirable in bioprocesses for the production of drugs and pharmaceuticals.

In the past, almost the whole biopharmaceutical production was carried out in stationary bioreactors in the form of stainless steel tanks. Traditionally, serum, usually fetal bovine serum, was used as a dietary supplement in order to promote cell growth.

However, the presence of serum in the production process impedes the so-called "downstream processing", i.e. the recovery and purification of the final products. Thus, since about ten years the manufacturers clearly aim at avoiding serum in cell cultures due to the easier "downstream processing". In addition, removing serum from the cell cultures results in an essential facilitation of the approval and certification of biopharmaceutical products. In approximately the same time period the pharmaceutical and biotechnological production in stationary steel tank facilities has clearly dropped, whereby more flexibility could be gained and installation time and manufacturing costs could be lowered. The problem of the "extended lag phase" was hardly observed in stationary facilities. Single-use cell culture containers do not show an "extended lag phase" in the presence of serum. However, the combination of single-use cell culture containers with serum-free media, which is increasingly applied in pharmaceutical and biotechnological manufacturing processes, is frequently affected by the occurrence of an "extended lag phase". However, said problem could not be solved up to now.

Thus, the object underlying the present invention is to eliminate the disadvantages of the single-use cell culture containers of the prior art. In particular, the object underlying the present invention is to provide single-use cell culture containers, which are sufficiently sterile and wherein an "extended lag-phase" does not occur or is at least largely reduced.

This object is achieved by a method for producing a single-use cell culture container, which is at least partially made of polymer material, wherein the cell culture container is treated with gamma radiation for sterilization, characterised in that the cell culture container is treated with inert gas before the treatment with gamma radiation. Thereby the amount of oxygen present can be selected such that during the treatment of the cell culture container with gamma radiation aldehydes and ketones are generated in an amount of at most 3 ppm.

Furthermore, the above mentioned object is achieved by a cell culture container which has been produced by the method according to the present invention.

BREIF DESCRIPTION OF THE DRAWINGS

DETAILED DESCRIPTION

Figure 1:
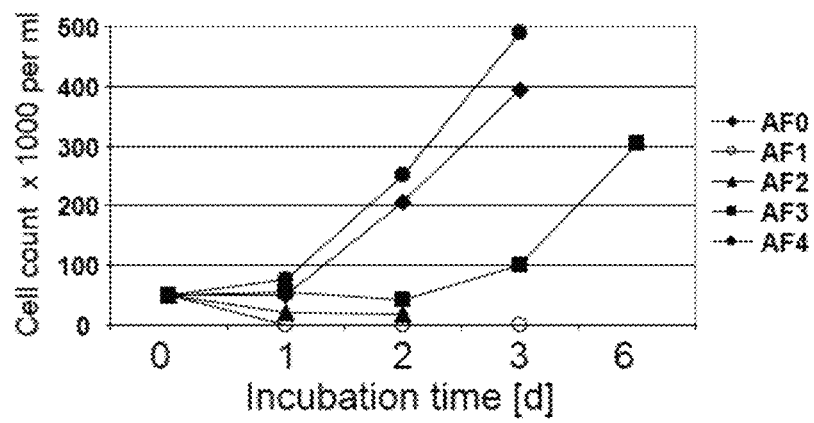
FIG. 1 is a graph of cell count versus incubation time showing relative rates of cell suspension of CHO AA8-luc cell growth in a medium, incubated with different amounts of acetone and formaldehyde, according to Example 1.

Surprisingly, the inventors have found that the treatment of the cell culture containers results in that aldehydes and ketones are formed and that these aldehydes and ketones are responsible for the described "extended lag phase". These aldehydes and ketones are obviously formed by a reaction of free radicals generated in the gamma irradiation with aerial oxygen. As will be shown further below and as can be derived from the experimental results and tables and graphs described below, said aldehydes and ketones formed in a corresponding concentration are clearly responsible for the extended lag phase.

By the treatment of the cell culture containers with inert gas before a gamma irradiation the forming of aldehydes and ketones can be inhibited. By inert gases, gases are meant which are very sluggish in reaction (inert), and thus participate only in very few chemical reactions. In the method according to the present invention nitrogen is preferably used as inert gas. However, also noble gases, particularly argon, or mixtures of noble gases and nitrogen, may be used as inert gas.

In a preferred embodiment of the present method the cell culture container is filled with inert gas before gamma irradiation and/or is introduced in a lockable container filled with inert gas before gamma irradiation. When filling the cell culture container with inert gas, the regular procedure will be to repeatedly fill the cell culture container with inert gas and drain the same, until it is finally filled a last time and drained such that a small amount of inert gas will remain in the container. This will guarantee the absence of aerial oxygen in the interior of the cell culture container. It is decisive that the cell culture container is treated with inert gas before a treatment with gamma radiation. However, it is preferred that the gamma irradiation will take place promptly after the treatment with inert gas. Preferably, the gamma irradiation for sterilization will be performed within 24 hours, for example, within 18 or 12 hours, after treatment with inert gas. This will secure optimal results concerning the cell growth in the cell culture container according to the present invention.

As mentioned above, the cell culture container according to the present invention may be introduced in a second container before irradiation with gamma radiation, in particular a bag, which contains inert gas. Both the cell culture container according to the present invention and said second bag preferably have gas barrier layers. A preferred cell culture container according to the present invention has an outer layer of polyethylene with a thickness of 0.1 to 0.5 mm as well as a further inner layer of polyethylene or EVA, which is contacted by the cell culture to be cultivated and also has a thickness of 0.1 to 0.5 mm. According to the present invention, the term "inner layer" refers to a layer, which is in contact with the cell culture to be cultivated, and the term "outer layer" refers to a further layer, which is different from said layer.

For example, the outer layer is a layer which is in contact with the environment, i.e. forms the outermost layer of the cell culture container.

A preferred cell culture container according to the present invention has an outer layer of polyethylene having a thickness of 0.15 to 0.35 mm as well as a further inner layer of polyethylene or EVA, which is contacted by the cell culture to be cultivated and also has a thickness of 0.15 to 0.35 mm. According to a particularly preferred embodiment of the present invention, the cell culture container has an outer layer of polyethylene having a thickness of 0.18 to 0.3 mm, for example, 0.2 mm, as well as a further inner layer of polyethylene or EVA also having a thickness of 0.18 to 0.3 mm, for example, 0.2 mm.

Preferably, a layer of ethyl-vinyl alcohol (EVOH), which serves as a gas barrier layer, is present between the two polyethylene layers. By said gas barrier layer a leakage of inert gas, which has been introduced in the cell culture container before a gamma irradiation, is prevented.

As already pointed out above, an "extended lag phase" is prevented by a complete exclusion of oxygen during the irradiation with gamma radiation. In addition, it has been surprisingly found that by the presence of small amounts of oxygen and thus by the presence of small amounts of aldehydes and/or ketones the cell growth can be optimized. Depending on the intensity of the gamma radiation, the polymer material of the cell culture container according to the present invention and the type of cells to be cultured, the irradiation with gamma radiation may be performed in the presence of 0% up to 20% oxygen. As already indicated above, in the presence of 0% oxygen an "extended lag phase" is reliably prevented and the cells can grow completely uncompromised.

Indeed, the cell growth can be enhanced in the presence of defined amounts of oxygen, which, however, have to be below the amount of oxygen present in air, by the generation of small amounts of aldehydes and ketones. In order to achieve this, the amount of oxygen present is selected such that during the irradiation with gamma radiation aldehydes and ketones are generated in a concentration of at most about 3 ppm. The undesired "extended lag phase" usually occurs at values of above 3 ppm.

In order to control such effects, in the method according to the present invention the cell culture container can be flushed with inert gas before irradiation with gamma radiation and supplied with inert gas and/or a defined amount of oxygen, which is below the oxygen content of the air. Thereby the generation of aldehydes and ketones and thus the occurrence of an "extended lag phase" may either be avoided, or a specific amount of aldehydes and ketones can be generated, such that the cell growth in the cell culture container is even improved.

Thus, in a specific embodiment the present invention relates to a method for sterilizing a single-use cell culture container, which is at least partially made of a polymer material, wherein the cell culture container is treated with inert gas before irradiation with gamma radiation in the above-described manner, in order to prevent the generation of aldehydes and ketones, which are responsible for the occurrence of an "extended lag phase", or in order to allow the generation of a specific amount of aldehydes and ketones, to thereby improve cell growth in the cell culture container.

According to the present invention, the irradiation with gamma radiation is preferably carried out in the presence of 18% oxygen or less, and more preferably 15% oxygen or less. According to a particularly preferred embodiment the irradiation with gamma radiation is carried out in the presence of 10% oxygen or less, for example, 8% or less. As already described above, besides the oxygen concentration, at which the irradiation with gamma radiation is carried out, also the intensity of the gamma radiation itself and the polymer material of the cell culture container according to the present invention as well as the type of cells to be cultivated influence the amount of generated aldehydes and ketones. According to a preferred embodiment, at irradiation doses of 25 to 50 kGy the oxygen content during the irradiation with gamma radiation is 0 to 15%, and according to a particularly preferred embodiment 0 to 10%. Further examples for a preferred oxygen content are ranges of 0.05 to 10%, 0.1 to 9% or 0.2 to 8%.

The above-mentioned generated aldehydes and ketones are in particular water-soluble aldehydes and ketones. Water-insoluble aldehydes and ketones have less effects on cell growth in the cell culture container according to the present invention, since lipophilic components having larger chain lengths do not intrude in the same amount into cell culture media, since said media usually contain water as the major component. According to the present invention, water-soluble aldehydes and ketones are those having a water-solubility of at least 30 g/l at 20° C.

Said aldehydes are particularly formaldehyde, acetaldehyde, and propionaldehyde. Said ketones are particularly acetone, butanone, methyl-propyl ketone as well as 3-pentanone.

The present invention also relates to a single-use cell culture container manufactured according to any one of the claims.

As already mentioned above, the cell culture container according to the present invention contains aldehydes and ketones, particularly water-soluble aldehydes and ketones at a concentration of at most 3 ppm.

Notably for applications in the drug sector, the cell culture container according to the present invention is preferably free of aldehydes and ketones, in particular of water-soluble aldehydes and ketones. According to the present invention, "free of aldehydes and ketones" means that the cell culture container according to the present invention contains aldehydes and ketones in an amount of 0 up to 0.01 ppm. In the drug sector aldehydes and ketones often have to be absent also due to directives of the Medicines Act. In this case the cell culture container according to the present invention will be sterilized with gamma radiation in the absence of oxygen.

In a further embodiment of the cell culture container according to the present invention the same contains aldehydes and ketones at a concentration of about 0.01 to about 3 ppm, in particular from 0.1 to 1 ppm. Surprisingly, in this range a particularly good cell growth can be observed.

As already mentioned above, the cell culture container according to the present invention is preferably formed as a multi-layer bag, which may comprise up to seven layers, for example, three layers. The different layers of the cell culture container according to the present invention can be manufactured of different materials or of the same materials, wherein the outer and the inner layers preferably consist of PE and/or EVA. In this configuration, it is further preferred that a layer different from the outermost and the innermost layer, which is designated in the following as an "intermediate layer", is a gas barrier layer, in particular an EVOH layer. According to a preferred embodiment, the cell culture container according to the present invention is formed as a three layer bag, wherein the inner and the outer layers preferably consist of PE or EVA and the intermediate layer is a gas barrier layer, in particular an EVOH layer.

Preferably, at least in an inner layer of the cell culture container according to the present invention UV stabilizers or so-called "anti-rads" are contained. "Anti-rads" are substances acting similar to UV stabilizers and prevent or reduce negative effects of the gamma radiation on a polymer material. Furthermore, these stabilizers also supress the generation of aldehydes and ketones by supressing the formation of radicals during irradiation with gamma radiation of the cell culture container according to the present invention. Examples for UV stabilizers are 2,6-di-tert-butylphenol and butyl-hydroxy toluene (BHT). Said examples do not limit the scope of the present invention in any manner. Furthermore, for the manufacturing of such cell culture containers a combination of two or more UV stabilizers and/or "anti-rads" may be used.

The UV stabilizers and anti-rads having sulfur or nitrogen molecules in the ring structure, which are usually used in polymer chemistry, cannot be used for an application of polymers in the cell culture despite their excellent effect, since sulfite and nitroso compounds, which have a strong cytotoxic effect, may be generated from these molecules by the effect of gamma radiation.

For different aldehydes and ketones the concentrations and concentration ranges in "ppm" provided herein partially result in opposing concentrations in mol/liter, which can be explained by the different molecular weight and the different densities of, for example, acetone and formaldehyde. Thus, the observed opposing tendency with regard to ppm and µM results in stating of concentration ranges, which by no means should be regarded to be excluding or absolute. Rather, said indications may refer to a concentration which ranges within +/−10% to 20% of the stated absolute limits.

As described above, the present invention is based in part on the finding that aldehydes and ketones, which are generated during irradiation with gamma radiation in a sterilizing method of a cell culture container, are responsible for the described "extended lag phase". Furthermore, the present invention is based on the finding that cell growth may be optimized in the presence of small amounts of oxygen and thus in the presence of small amounts of aldehydes and/or ketones. Thereby it is possible to allow a more effective cell cultivation. Thus, the present invention also provides a method for cell cultivation, wherein water-soluble aldehydes and/or ketones selected from the group consisting of formaldehyde, acetaldehyde, propionaldehyde, acetone, butanone, 2-pentanone, and 3-pentanone are added to a cell suspension in a concentration from about 0.01 to 3 ppm, preferably from 0.1 to 1 ppm.

EXAMPLES

1. Verification of the Influence of Aldehydes and Ketones on Cell Growth:

Five samples of a cell suspension of CHO AA8-luc cells (Chinese hamster ovary cells) and a medium (FMX-8), wherein the composition of the medium is given in table 1, were incubated with different amounts (broad concentration range) of acetone and formaldehyde. FIG. 1 shows the different cell growth:

AF0 is a control without any addition of acetone or formaldehyde (=FMX-8 medium). Here a normal, non-disturbed cell growth can be observed.

AF1 corresponds to 250 ppm acetone and 250 ppm formaldehyde (corresponds to 4.3 mM acetone and 8.325 mM formaldehyde). At this concentration all cells die.

AF2 corresponds to 25 ppm acetone and 25 ppm formaldehyde (corresponds to 430 µM acetone and 832.5 µM formaldehyde). Also in this case all cells die.

AF3 corresponds to 2.5 ppm acetone and 2.5 ppm formaldehyde (corresponds to 43 µM acetone and 83.25 µM formaldehyde). In this case an "extended lag phase" is clearly visible.

AF4 corresponds to 0.25 ppm acetone and 0.25 ppm formaldehyde (corresponds to 4.3 µM acetone and 8.325 µM formaldehyde). In this case an increased cell growth can be observed.

The two crucial curves are AF3 and AF4. These conditions clearly demonstrate the different effect of aldehyde and ketone on cell growth. If the amount of added acetone/formaldehyde is small, compared to the control AF0 (absence of aldehyde and ketone), an improved growth is found. With AF3 the "extended lag phase" is clearly visible, which is frequently found with the cell culture containers of the prior art. In general, during irradiation with gamma radiation an amount of aldehydes and ketones is generated, which is in the range of AF3. In this case, only an extremely small cell growth can be observed during the first three to four days of incubation time of the cell cultures. Only after the third day the cell growth is enhanced. This phenomenon is called "extended lag phase".

Figure 2:
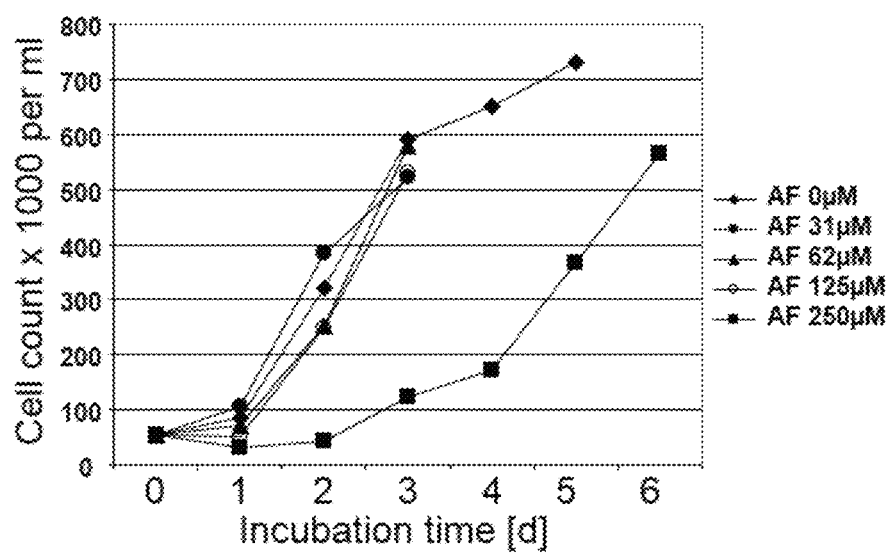
FIG. 2 is a graph of cell count versus incubation time showing the results of a further run with five different cell culture preparations, which demonstrates the growth-promoting effect of aldehydes and ketones.

FIG. 2 shows the results of a further run with five different cell culture preparations having different concentrations (narrow concentration range) of acetone and formaldehyde.

In order to check the growth promoting action of small amounts of aldehydes and ketones, an additional experimental series was performed, which is summarized in FIG. 2. Here, inter alia an amount of 31.25 µM of formaldehyde and acetone was added to a cell suspension of CHO-luc cells. This corresponds to a concentration of about 1 ppm of aldehydes and ketones. In view of the control, wherein no aldehyde or ketone has been added, said cell sample shows an increased growth, which demonstrates the growth-promoting effect of aldehydes and ketones in a concentration of about 1 ppm for suspension cell cultures over a broad concentration range in addition to the results from the first experiment.

0 is Control (=FMX-8 medium)>>normal growth 31.25 μM acetone (=1.82 ppm) and 31.25 μM formaldehyde (=0.94 ppm)>>increased growth 62.5 μM acetone (=3.64 ppm) and 62.5 μM formaldehyde (=1.88 ppm)>>no effect 125 μM acetone (=7.28 ppm) and 125 μM formaldehyde (=3.76 ppm)>>no effect 250 μM acetone (=14.56 ppm) and 250 μM formaldehyde (=7.52 ppm)>>extended lag phase Due to the difference in molecular weight and the difference in specific density of acetone and formaldehyde, an opposing tendency for ppm and μM is observed.

2. Determination of the Amount of Aldehydes and Ketones Generated by Irradiation of Cell Culture Containers with Gamma Radiation:

A culture bag to be tested was filled with 0.5 ml of distilled water per $cm^2$ of the bag inner surface. The water was left in the bag for 24 h. After that the amount of generated water-soluble aldehydes and ketones was measured. With this method all water-soluble aldehydes and ketones can be detected. The measurement of aldehydes and ketones can, for example, be carried out with GC-MS.

3. Comparison of Cell Growth in Differently Treated Cell Culture Bags:

A PE film (0.2 mm thickness) was heat-welded to obtain bags (inner layer surface area about 100 $cm^2$). The bags were filled 3× with air, oxygen ($O_2$) or nitrogen ($N_2$), respectively, and drained such that a small amount of the gas remained in the bag. Subsequently the bags were placed in 50 ml centrifuge tubes made of PP, these tubes were filled 3× with air, $O_2$ or $N_2$ and tightly closed. Then the bags were treated with 50 kGy of gamma radiation. After the irradiation the bags were each filled with 5 ml of FMX-8 medium in a sterile manner and incubated for 24 h at 37° C.

The medium was removed by suction from the respective bags and 1.5 ml each was added to a cell suspension of 1.5 ml each at a 1:10 dilution, resulting in a starting cell number of 50,000 per ml at the beginning of the incubation. The cells were incubated for 4 days at 37° C. and 5% $CO_2$ and then counted.

Figure 3:
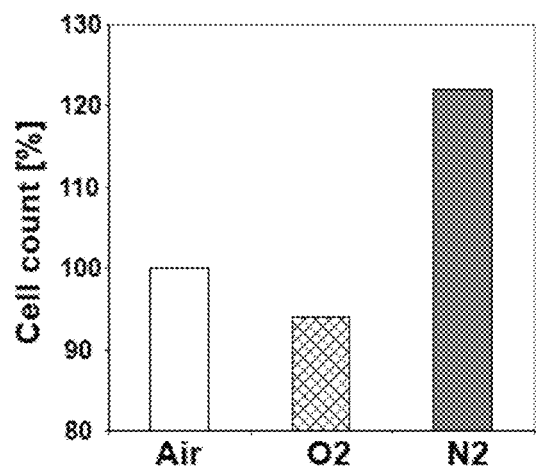

FIG. 3 shows the cell growth, wherein the medium from the bag treated with air was used as a control defined to be 100%. A treatment of bags with oxygen results in a reduced cell growth. A treatment of the bags with $O_2$ results in a delay of the cell growth. A treatment with $N_2$ results in an improvement of the cell growth. As compared to bags treated with air or pure oxygen only very few aldehydes and ketones are generated (see FIG. 3).

Figure 4:
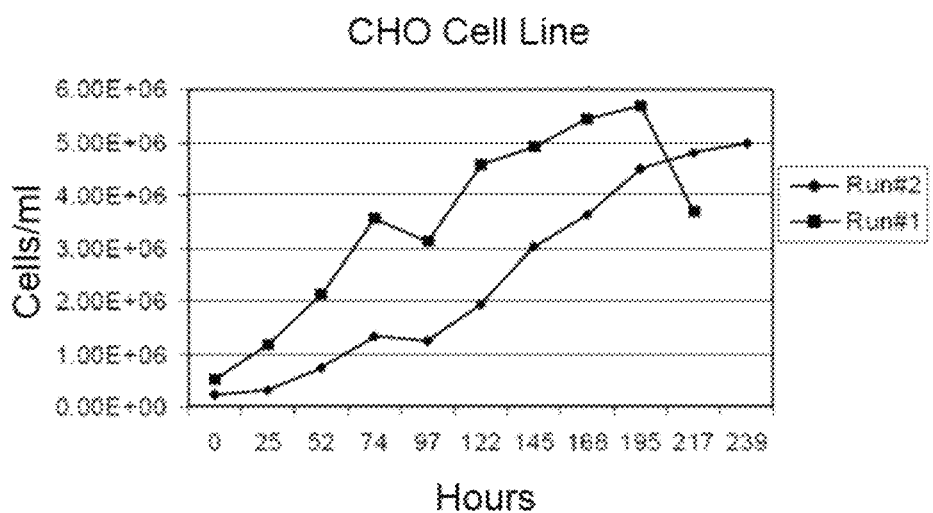

FIG. 4 shows the cell growth in two different cell culture containers of polyethylene, which have both been treated with gamma radiation before filling the same with cell suspensions. The two shown cell culture containers are from the same batch of containers, which have been simultaneously treated with gamma radiation in an irradiation device. The container labelled as run #2 shows a clear "extended lag phase". In the cell culture container designated run #1 this effect is less clear. In the following example this is due to the fact that the container from run #2 was lying on top during irradiation and thus has been in contact with the greatest amount of aerial oxygen. Thus, in this cell culture container much more aldehydes and ketones have been generated as in the run#1 container, which was placed further down during the irradiation process and thus has come into contact with less aerial oxygen. This phenomenon, which is regularly observed in the production of cell culture containers, could not be explained or eliminated until now.

The invention claimed is:

1. A method for producing a single-use cell culture container, which is at least partially made of polymer material, wherein the cell culture container has an outer layer of polyethylene with a thickness of 0.1 to 0.5 mm as well as an inner layer of polyethylene or EVA, which is contacted by the cell culture to be cultivated and has a thickness of 0.1 to 0.5 mm, wherein the cell culture container is treated with gamma radiation for sterilization at irradiation doses of 25 to 50 kGy, characterized in that the cell culture container is treated with inert gas before the treatment with gamma radiation, whereby the amount of oxygen present is selected such that, during the treatment of the cell culture container with gamma radiation, aldehydes and ketones are generated in a concentration of about 0.1 to about 3 ppm, and wherein the treatment with gamma radiation is carried out in the presence of 1.0 to 15% oxygen.

2. The method according to claim 1, characterized in that the cell culture container is filled with inert gas before gamma radiation treatment and/or introduced in a lockable container filled with inert gas before gamma radiation treatment.

* * * * *